United States Patent [19]

Hone et al.

[11] 4,007,106
[45] Feb. 8, 1977

[54] DEVICE FOR MEASURING OXYGEN CONCENTRATION IN MOLTEN-METAL

[75] Inventors: Michel Hone, St. Placide, Canada; Serge Houot, Lambersart, France

[73] Assignee: Canadian Patents and Development Limited, Ottawa, Canada

[22] Filed: Aug. 18, 1975

[21] Appl. No.: 607,195

Related U.S. Application Data

[63] Continuation-in-part of Ser. No. 449,994, March 11, 1974, abandoned.

[30] Foreign Application Priority Data

June 22, 1973 Canada .............................. 174777

[52] U.S. Cl. .............................. 204/195 S; 204/15
[51] Int. Cl.$^2$ ........................................ G01N 27/46
[58] Field of Search ........................... 204/195 S, 15

[56] References Cited
UNITED STATES PATENTS

| | | | |
|---|---|---|---|
| 3,046,786 | 7/1962 | Tessem | 204/195 R |
| 3,378,478 | 4/1968 | Kolodney et al. | 204/195 S |
| 3,400,054 | 9/1968 | Ruka et al. | 204/195 S |
| 3,752,753 | 8/1973 | Fitterer | 204/195 S |
| 3,776,831 | 12/1973 | Roy | 204/195 S |
| 3,791,954 | 2/1974 | Noda et al. | 204/195 S |
| 3,838,021 | 9/1974 | Arbiter | 204/195 S |
| 3,864,231 | 2/1975 | Richardson | 204/195 S |
| 3,864,232 | 2/1975 | Handman et al. | 204/195 S |

*Primary Examiner*—T. Tung
*Attorney, Agent, or Firm*—Edward Rymek

[57] ABSTRACT

The present invention is directed to an improved method of measuring oxygen concentration in molten metal using the galvanic oxygen concentration cell method. It consists of providing a layer of inert gas between the cell electrolyte and the melt, this prevents contamination of the electrolyte while at the same time allows it to be in thermal and chemical equilibrium with the melt, resulting in continuous measurements of oxygen activity from which oxygen concentration may be calculated. Novel probes are disclosed which include a solid electrolyte oxygen concentration cell, a cavity for containing the inert gas adjacent the cell electrolyte to prevent contact between it and the molten metal and a thermocouple for temperature measurements.

7 Claims, 3 Drawing Figures

DEVICE FOR MEASURING OXYGEN CONCENTRATION IN MOLTEN-METAL

This application is a continuation-in-part of U.S. Ser. No. 449,994, filed Mar. 11, 1974, now abandoned.

This invention relates to the continuous measurement of the activity, and hence concentration of oxygen dissolved in molten metals by making use of a galvanic oxygen concentration cell having a solid electrolyte.

Many probes have been developed, which use the above galvanic oxygen concentration cell principle, examples of which are described in U.S. Pat. No. 3,619,381, Fitterer, issued Nov. 9, 1971; U.S. Pat. No. 3,657,094, Hans, issued Apr. 18, 1972 and assigned to Centre National de Recherches Metallurgique; Canadian Pat. No. 915,262, Richards et al, issued Nov. 21, 1972 and assigned to The Broken Hill Proprietary Company; as well as Canadian Pat. No. 917,253, Faurschou et al issued Dec. 19, 1972 and assigned to Her Majesty in right of Canada. These probes though effective for short periods are unable to provide continuous output readings since they are either destroyed by thermal shock as it is required that they be plunged into the molten metal quickly, or they are debilitated by contamination of the electrolyte which is in direct contact with the molten metal.

It is therefore an object of the present invention to provide a method of measuring oxygen dissolved in molten metals on a continuous basis.

A further object of this invention is to provide a method of measuring oxygen dissolved in molten metals which will allow the probe to be eased into the liquid, thus avoiding thermal shock to the solid electrolyte.

Yet another object of this invention is to provide an improved probe for measuring oxygen dissolved in molten metals by reducing to a minimum the potential for damage to the solid electrolyte and subsequent malfunctioning of the probe.

These and other objects are achieved by maintaining an inert gas atmosphere such as argon between the electrolyte in the oxygen probe and the molten metal when the probe is inserted into molten metal such as iron, steel, nickel, copper, etc. or their alloys, to make measurements.

To achieve this, the probe may consist of a solid oxygen reference such as a mixture of molybdenum and molybdenum oxide in contact with a solid electrolyte such as stabilized zirconia and enclosed in a tube made of nonelectrical conductive material such as "Vycor", a trademark for a high silica glass (96% $SiO_2$) having a softening temperature of approximately 1500° C. This tube is fixed within a second tube in such a manner as to define a cavity below the electrolyte. An electrode is located in the surface of the electrolyte facing the oxygen reference and a thermocouple is located in the surface of the electrolyte facing the cavity, with one of the thermocouple leads acting as the second electrode by which the oxygen concentration cell emf is measured.

As the probe is lowered over the molten metal, the speed being dependent on the thermal shock resistance of the materials used in the manufacture of the probe, the argon, or other inert gas is forced from an inert gas source into the cavity through the "Vycor" tube. The heat from the melt fuses the "Vycor" tube to the tube defining the cavity as well as to the electrolyte. At this point the flow of argon between the electrolyte and the "Vycor" is blocked. This is immediately sensed by a potentiometer since the reference pressure of oxygen is much lower than the partial pressure of oxygen in the inert gas of the cavity. The probe is then lowered into the melt where it is allowed to come to thermal and chemical equilibrium with the melt. Since the argon prevents direct contact between the molten metal and the electrolyte or the thermocouple embedded in its surface, continuous readings of oxygen cell and thermocouple emf's can be made over a relatively long period of time thus continuously indicating the oxygen content and temperature of the molten metal.

Alternately, the cavity below the solid electrolyte in the probe may be constructed containing the inert gas. The cavity may be a gas tight, capped cavity filled with sufficient inert gas such that when the cap disintegrates or melts as the probe is lowered into the molten metal, the gas will prevent contact between the molten metal and the electrolyte. Or again, a small enclosure such as a capsule, which contains inert gas under pressure may be fixed within the cavity and constructed so as to rupture and release the inert gas into the cavity preventing contact between the molten metal and electrolyte when the probe is lowered into the molten metal.

Figure 1:
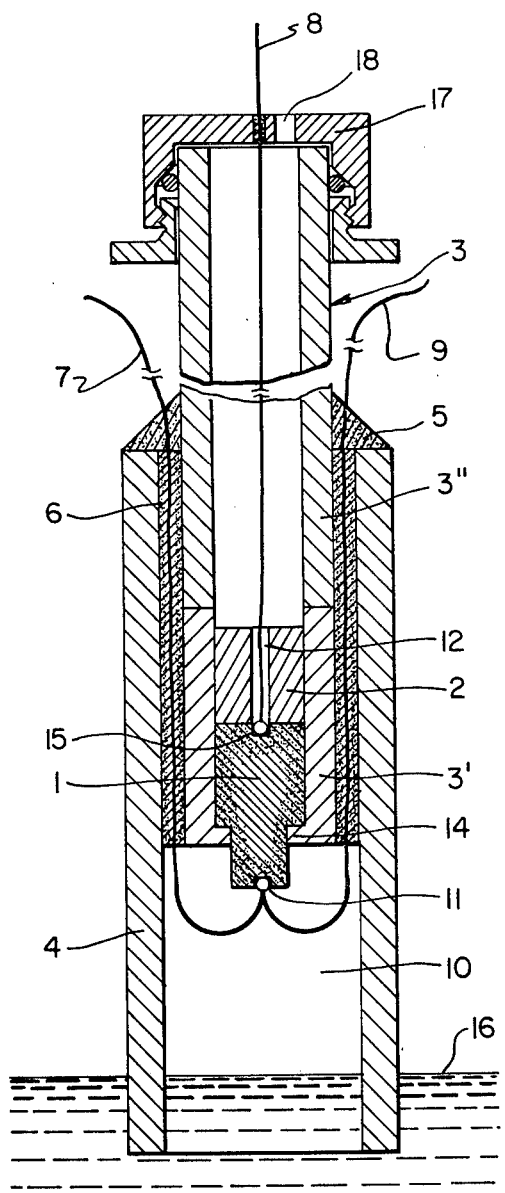
FIG. 1 is a sectional view of one embodiment of a probe in accordance with the invention.

In the galvanic oxygen concentration cell method of measuring oxygen dissolved in molten metals, the relation between the emf of the cell and the activity of oxygen in the condensed phase in determined by a virtual thermodynamic process involving the transfer of one mole of oxygen from the reference electrode to the condensed phase. The process steps involved and the corresponding variations of Gibbs free energy ($\Delta G$) are as follows:

$$O_2(P_1) = O_2(P_2) \qquad \Delta G_1 = RT \ln \frac{P_2}{P_1} \quad (1)$$

$$O_2(P_2) = O_2(1 \text{ atm.}) \qquad \Delta G_2 = RT \ln \frac{1}{P_2} \quad (2)$$

$$O_2(1 \text{ atm.}) = 2\underline{O}(h_0\ 1) \qquad \Delta G_3 = \Delta G^\circ \quad (3)$$

$$2\underline{O}(h_0\ 1) = 2\underline{O}(h_0) \qquad \Delta G_4 = RT \ln \frac{h_0^2}{1} \quad (4)$$

Therefore for the entire process; adding (1), (2), (3) and (4);

$$O_2(P_1) = 2\underline{O}(h_0) \quad \Delta G = RT \ln \frac{h_0^2}{P_1} + \Delta G^\circ \quad (5)$$

Dividing (5) by $-nF$ $$E = \frac{RT}{nF} \ln \frac{P_1}{h_0^2} - \frac{\Delta G^\circ}{nF} \quad (6)$$

where:

$P_1$ = reference oxygen pressure (atm.)

$P_2$ = partial pressure of oxygen in inert gas cavity (atm.)

$h_O$ = Henrian activity of oxygen

ΔG = Gibbs free energy change (cal./mole)
ΔG° = standard Gibbs free energy change (cal./mole)
R = Universal gas constant (cal./mole/°K)
T = temperature (°K)
n = number of electrons involved in the reaction
F = Faraday constant
E = emf of the cell (v.)

Since all of the parameters of the equation 6 are known except for E, T and $h_O$, $h_O$ may be determined on a continuous basis by providing a probe which will generate continuous readings of E, the oxygen cell emf, and T, the melt temperature. The oxygen concentration in wt% 0 can be calculated from the activity $h_O$ by means of the relation $$0 = \frac{h_o}{f_o}$$

where $f_O$ is the activity coefficient for the system.

FIG. 1 shows the construction of one embodiment of the probe in accordance with the invention. It consists of a tube 3 with an approximate I.D. of 7 mm made of electrical insulating material, having a lip 14 formed on the interior edge of one end. This tube 3 must also have a high thermal shock resistance and thus may be made of "Vycor" or some such similar material. However, in order to give more rigidity to tube 3 and to prevent creep at high temperatures, a short length of "Vycor" 3', approximately 2 cm long, may be joined to more heat-resistant material 3'' such as quartz as shown in FIG. 1, to form a complete tube 3 which could be approximately 0.5 meters long. However, these dimensions would vary for different applications. The heat resistant material must be sufficiently strong at the operating temperature of the probe to support it for a prolonged period of time. A solid electrolyte 1, such as a stabilized zirconia rests on lip 14 in the interior of tube 3. A solid reference electrode material 2, such as a mixture of molybdenum and molybdenum oxide, is in intimate contact with the electrolyte 1 within tube 3.

The solid reference electrode is preferably used rather than a gaseous reference to prevent cooling of the cell by circulating gases, allowing a stable thermal equilibrium to obtain between the probe and the molten metal and, more importantly, because of the low partial pressure of oxygen which obtains from a reference of this type, thereby reducing to a minimum leakage currents through the electrolyte.

The electrolyte 1 and the oxygen reference 2 fit loosely within tube 3 until the probe is lowered above the molten metal prior to immersion, at which time they will bond into place by the fusion action of the "Vycor" tubing. This arrangement provides advantage when the probe is manufactured as it simplifies the assembling procedure and results in lower costs.

The end of a lead 8, made of conducting material such as platinmum wire, is fused into a ball 15 which is mechanically embedded into a small cavity in the upper surface of the electrolyte 1 as shown in FIG. 1, forming one electrode of the oxygen cell. Lead 8 runs upward through tube 3 via a hole 12 in the oxygen reference material 2 and out of the upper end of the probe through a gas tight cap 17. Cap 17 includes an opening 18 by which the inert gas 1 such as argon is pumped into the probe.

The junction of an appropriate thermocouple 11 such as Pt-Rh 10% is mechanically embedded into a small cavity in the lower surface of the electrolyte pellet, this allows one of the thermocouple leads 7, 9 to be used as the second electrode for the oxygen cell.

A second tube 4 fits loosely over tube 3 defining a cavity 10 below electrolyte 1. Tube 4 may be made out of "Vycor", quartz, alumina or any appropriate material which will not melt at the high operating temperatures or will not dissolve into the melt. Leads 7 and 9 are located in the space between the walls of tubes 3 and 4 and the space is filled with a cement 6, such as alundum. In addition, a cement 5 which could consist of powdered "Vycor" and alumina in proportions to form mullite, may be placed around tube 3 at the top of tube 4. This provides a seal which is formed rapidly by the high temperature as the probe is lowered over the melt, thus preventing the escape of the inert gas from cavity 10.

Finally, if desired, a thin cap, not shown in FIG. 1 and consisting of a material which will disintegrate or melt in the molten metal, may be placed over the cavity opening formed by tube 4 to prevent slag or such from being trapped within the cavity 10 as the probe is lowered into the molten metal.

In operation, as the probe is lowered into the molten metal 16, inert gas from an inert gas source is forced into opening 18 at the top of the probe. The gas will flow down into cavity 10 since the electrolyte 1 and oxygen reference 2 fit loosely within tube 3. After the tubes 3 and 4 and the electrolyte 1 and oxygen reference 2 are bonded by the high temperatures, the inert gas is trapped within the cavity and further flow of gas through the probe is ceased. For normal operation, the probe is placed in the molten metal 16 as shown in FIG. 1 such that the end of the outer tube 4 is well below the surface, however pellet 1 need not be below the molten metal surface. It is desirable that the argon provide a distance of approximately 1 to 2 cm between the electrolyte pellet 1 and the surface of the melt 16 within the cavity. The inert gas within the cavity 10 prevents the molten metal from coming into contact with the electrolyte 1. However, the oxygen cell will still operate normally producing an emf across the electrolyte 1 which can be detected across leads 7 and 8, since at the temperature of the melt, an equilibrium is quickly reached between oxygen in the inert gas atmosphere and oxygen in the molten metal whereby the partial pressure of the oxygen in the inert gas will be directly proportional to the square of the effective concentration of dissolved oxygen in the molten metal. In addition, the probe achieves thermal equilibrium with the molten metal such that the thermocouple 11 will produce an emf proportional to the temperature of the melt. This emf will be detected across leads 7 and 9.

Since the argon prevents the electrolyte and the thermocouple from becoming contaminated by the molten metal, it is found that the probe will operate effectively for several hours, continuously monitoring oxygen activity and thus oxygen concentration in the melt.

Figure 2:
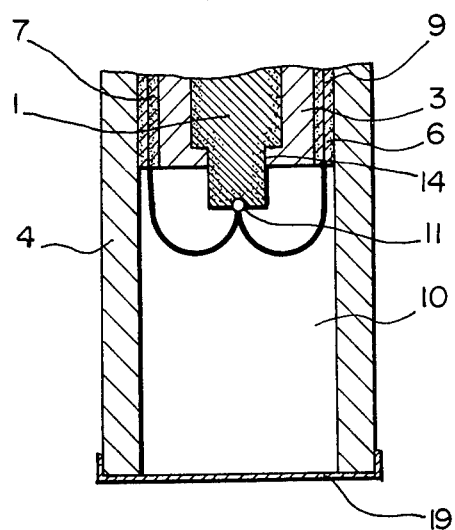
FIG. 2 is a sectional view of the cavity structure of a second embodiment.

FIG. 2 illustrates the lower section of a probe similar to that described with respect to FIG. 1, including tube 3, the solid electrolyte 1 positioned on lip 14, thermocouple 11 with leads 7 and 9, and the second tube 4 cemented to tube 3 by cement 6 to form a cavity 10 adjacent the electrolyte 1. In this embodiment however, the electrolyte 1 is sealed within tube 3, and tube 3 is sealed within tube 4 such that gas in the cavity is unable to move up into the probe. This probe further includes a tight-fitting cap 19 which is positioned over the cavity opening. If it is desired to flush the cavity 10 with inert gas just before use of the probe, the cap 19 need not be gas-tight as the inert gas will not escape before the probe is inserted in the molten metal. However, if it is desired to store the inert gas in cavity 10 at or above atmospheric pressure, it is required that cap 19 be sealed to tube 4 so as to prevent its escape. Cap 19 is made from a material which will contain the gas within the cavity and which will melt or dissolve when the probe is inserted into the molten metal. This cap could be made of a material having the same chemistry as the metal being tested or having a lower melting point.

Figure 3:
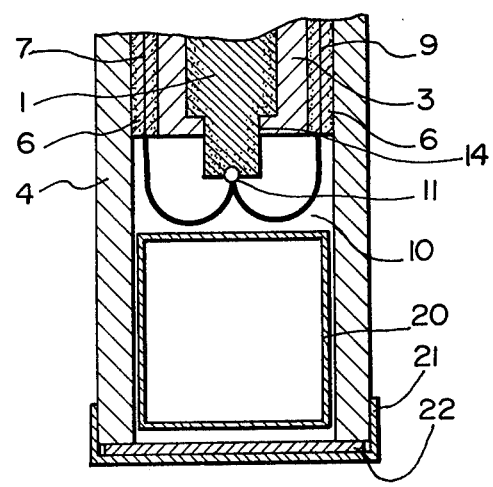
FIG. 3 is a sectional view of the cavity structure of a third embodiment.

FIG. 3, as in FIG. 2, illustrates the lower section of a probe similar to that described with respect to FIG. 1, including tube 3, the solid electrolyte 1 positioned on lip 14, thermocouple 11 with leads 7 and 9, and the second tube 4 cemented to tube 3 by cement 6 to form a cavity 10 adjacent the electrolyte 1. Once again, as in FIG. 2, the cavity 10 is gas tight at the tube 3-tube 4 interface and at the tube 3-electrolyte 1 interface. A source of inert gas such as a capsule 20 filled with inert gas at or above atmospheric pressure is positioned within the cavity 10. It may be tight fitting or attached to the inner wall. The capsule 20 may be made of "Vycor" or some such material which will rupture under the pressure of the inert gas in the capsule which expands due to the heat when the probe is lowered over the molten metal. The gas is thus released into the cavity 10.

On the other hand, it may be made of material such as plastic which will disintegrate due to the heat of the melt. In this case, it may be preferable to enclose the open end of the cavity 10 with a tight fitting cap 21 having an insulating disc 22 which covers the open end of the cavity 10. When the probe is lowered into the molten metal, the cap 21 will melt releasing the insulating disc 22. The plastic capsule 20 will then rupture and disintegrate allowing the expanding inert gas to fill the cavity 10. Any excess inert gas will bubble through the bath. Either of the above capsule sources provides entrapped inert gas in cavity 10 which prevents actual contact between the electrolyte 1 and the molten metal.

We claim:

1. A probe for determining the concentration of oxygen in a molten metal comprising:
    a thermal shock resistant and electrical insulating tube having first and second ends;
    a solid electrolyte loosely mounted at the second end of the tube to allow an inert gas injected into the first end of the tube to flow between the tube wall and the electrolyte, out of the second end of the tube, the tube and the electrolyte being adapted to fuse to form a gas tight seal when the probe is lowered into the molten metal;
    cavity means located at the second end of the tube containing sufficient inert gas to prevent the actual contact between the electrolyte and the molten metal as the probe is lowered into the molten metal; and
    a solid oxygen reference located within the tube in contact with the electrolyte and a pair of electrodes mounted across the electrolyte by which the emf across the electrolyte is detected.

2. A probe as claimed in claim 1 wherein said cavity means comprises an outer thermal shock resistant tube loosely mounted over a portion of the insulating tube and extending beyond the end of the insulating tube, and a cement provided between the insulating tube and the outer tube, said cement being adapted to produce a gas tight seal between the insulating tube and the outer tube when the probe is lowered into the molten metal.

3. A probe for determining the concentration of oxygen in a molten metal comprising:
    a thermal shock resistant and electrical insulating tube having first and second ends;
    a source of inert gas connected to said first end;
    a solid electrolyte loosely mounted at the second end of the tube to allow an inert gas injected into the first end of the tube to flow between the tube wall and the electrolyte, out of the second end of the tube, the tube and the electrolyte being adapted to fuse to form a gas tight seal when the probe is lowered into the molten metal;
    cavity means located at the second end of the tube, said cavity means being adapted to contain sufficient inert gas to prevent the actual contact between the electrolyte and the molten metal as the probe is lowered into the molten metal; and
    a solid oxygen reference located within the tube in contact with the electrolyte and a pair of electrodes mounted across the electrolyte by which the emf across the electrolyte is detected.

4. A probe for determining the concentration of oxygen in a molten metal comprising:
    a thermal shock resistant and electrical insulating tube having first and second ends;
    a solid electrolyte mounted at the second end of the tube forming a gas tight seal between the tube and the electrolyte;
    cavity means, located at the second end of the tube, containing sufficient inert gas to prevent the actual contact between the electrolyte and the molten metal as the probe is lowered into the molten metal;
    an oxygen reference located within the tube in contact with the electrolyte; and
    a pair of electrodes mounted across the electrolyte by which the emf across the electrolyte is detected.

5. A probe as claimed in claim 4 wherein said cavity means comprises:
    an outer thermal shock resistant tube mounted over a portion of the insulating tube and extending beyond the end of the insulating tube, with a cement between the insulating tube and the outer tube, to produce a gas tight seal between the insulating tube and the outer tube;
    a cap mounted over the open end of said outer tube for maintaining inert gas within the cavity, said cap being adapted to melt or dissolve when lowered into the molten metal.

6. A probe as claimed in claim 4 which further includes a source of inert gas mounted within the cavity means, the source being adapted to rupture, releasing the inert gas into the cavity means when the probe is lowered over the molten metal.

7. A probe as claimed in claim 6 wherein said source consists of a plastic capsule positioned within said cavity and the probe further includes an insulated cap mounted over the open end of said outer tube for protecting the capsule until the probe is lowered into the molten metal.

* * * * *